United States Patent
Arditi et al.

(10) Patent No.: US 8,036,437 B2
(45) Date of Patent: Oct. 11, 2011

(54) PERFUSION ASSESSMENT METHOD AND SYSTEM BASED ON ANIMATED PERFUSION IMAGING

(75) Inventors: Marcel Arditi, Geneva (CH); Nicolas Rognin, Geneva (CH); Peter Frinking, Geneva (CH)

(73) Assignee: Bracco Research SA, Geneva (CH)

( * ) Notice: Subject to any disclaimer, the term of this patent is extended or adjusted under 35 U.S.C. 154(b) by 1030 days.

(21) Appl. No.: 11/918,589

(22) PCT Filed: Apr. 13, 2006

(86) PCT No.: PCT/EP2006/061578
§ 371 (c)(1),
(2), (4) Date: Oct. 15, 2007

(87) PCT Pub. No.: WO2006/108868
PCT Pub. Date: Oct. 19, 2006

(65) Prior Publication Data
US 2009/0028406 A1     Jan. 29, 2009

(30) Foreign Application Priority Data
Apr. 14, 2005 (EP) .................................. 05102960

(51) Int. Cl.
*G06K 9/00* (2006.01)
(52) U.S. Cl. ............ 382/128; 382/130; 702/19; 702/22; 702/179; 702/181; 600/440; 600/438; 600/458; 600/443; 600/437
(58) Field of Classification Search .................. 382/128, 382/130, 131, 132; 702/19, 22, 179–181; 600/440, 438, 458, 443, 437
See application file for complete search history.

(56) References Cited

U.S. PATENT DOCUMENTS

| 5,743,266 A | * | 4/1998 | Levene et al. | 600/458 |
| 6,419,632 B1 | * | 7/2002 | Shiki et al. | 600/443 |
| 2003/0114759 A1 | * | 6/2003 | Skyba et al. | 600/458 |

FOREIGN PATENT DOCUMENTS

| WO | WO 02/056666 | * | 7/2002 |
| WO | WO2004/110279 | | 12/2004 |

OTHER PUBLICATIONS

Ultrasonic Enhancement of alpha and beta expressing cells with targeteed contrast agents; Dayton et al ; 2003 IEEE.*
Targeted Ultrasonic Contrast Agents for molecular Imaging andTherapy; Ianza et al. (Jul./Aug. 2001).*

* cited by examiner

*Primary Examiner* — Wesley Tucker
(74) *Attorney, Agent, or Firm* — Dylan O. Adams; Graybeal Jackson LLP

(57) ABSTRACT

An embodiment of a medical imaging system is proposed. The system includes means for providing a sequence of recorded input images each one offering a digital representation at a corresponding instant of a body part being perfused with a contrast agent, each input image including a plurality of visualizing values each one representing a corresponding portion of the body part, and means for associating each sequence of corresponding sets in the input images of at least one visualizing value with a model function of time; the system further includes means for generating a sequence of computed images at further instants, each computed image including a plurality of further visualizing values each one being determined by an instantaneous function-value which is calculated from the associated model function at the corresponding further instant, and means for displaying the sequence of computed images.

23 Claims, 8 Drawing Sheets

PERFUSION ASSESSMENT METHOD AND SYSTEM BASED ON ANIMATED PERFUSION IMAGING

PRIORITY CLAIM

This application claims priority from PCT/EP2006/061578, published in English, filed Apr. 13, 2006, which claims priority from European patent Application No. 05102960.1, filed Apr. 14, 2005, which are incorporated herein by reference.

TECHNICAL FIELD

An embodiment of the present invention relates to the medical imaging field. More specifically, an embodiment of the present invention relates to the display of animated perfusion images.

BACKGROUND

Medical imaging is a well-established technique in the field of equipment for medical applications. Particularly, this technique is commonly exploited for the assessment of blood perfusion, which finds use in several diagnostic applications and especially in ultrasound analysis. For this purpose, an ultrasound contrast agent (UCA), for example, consisting of a suspension of phospholipid-stabilized gas-filled microbubbles, is administered to a patient. The contrast agent acts as an efficient ultrasound reflector, so that it can be easily detected by applying ultrasound waves and recording a resulting echo signal. As the contrast agent flows at the same velocity as the blood in the patient, its tracking provides information about the perfusion of the blood in a body part to be analyzed.

Typically, the flow of the contrast agent is monitored by acquiring a sequence of consecutive images representing the body part during the perfusion process. More in detail, the value of each pixel of the images indicates an intensity of the recorded echo signal for a corresponding portion of the body part. In this way, the sequence of images depicts the evolution over time of the echo signal throughout the body part. Therefore, the analysis of this sequence of images (for example, displayed on a monitor) provides a quantitative indication of the blood perfusion in the body part.

However, the quality of the images that are displayed is often quite poor. Indeed, the value of each pixel of the images exhibits large variations in time. Moreover, the inevitable presence of speckle grains in the images produces distracting patterns. The quality of the images is also adversely affected by any motion of the body part during acquisition. Another factor that hinders an effective analysis of the images is the background echo signals that are superimposed to the useful information. All of the above makes it very difficult to establish a correct assessment of the perfusion process; in any case, the results obtained are strongly dependent on the skill of an operator who acquires and/or analyzes the sequence of images.

Some attempts have been made to improve the quality of the images in specific applications. For example, U.S. Pat. No. 6,676,606, which is incorporated by reference, proposes a solution for facilitating the identification of tiny blood vessels in the body part. For this purpose, the images are processed to reduce the contribution of pixels that are the same from image to image (for example, associated with stationary tissues) and to make persistent the pixels that instead change from image to image (for example, due to a moving microbubble). This enhances the visualization of micro-vascular structures.

On the other hand, a quantitative assessment of the perfusion process is provided by parametric analysis techniques. In this case, the intensity of the echo signal that is recorded over time (for each single pixel or group of adjacent pixels) is fitted by a mathematical model function. The model function can then be used to calculate different perfusion parameters, which are indicative of corresponding morphological characteristics of the respective portion of the body part. This technique has been proposed for the first time in Wei, K., Jayaweera, A. R., Firoozan, S., Linka, A., Skyba, D. M., and Kaul, S., "Quantification of Myocardial Blood Flow With Ultrasound-Induced Destruction of Microbubbles Administered as a Constant Venous Infusion," Circulation, vol. 97, 1998, which is incorporated by reference. For example, in a so-called destruction-replenishment technique (wherein the contrast agent is destroyed by a flash of sufficient energy, so as to observe its reperfusion following destruction), a commonly accepted model is defined by a mono-exponential function I(t) of the intensity of the (video) echo signal against the time, with a general form:

$$I(t)=A \cdot (1-e^{-\beta t})$$

where A is a steady-state amplitude and $\beta$ is a velocity term of the mono-exponential function (with the time origin taken at the instant immediately following the destruction flash). In this case the perfusion parameters are the values A and $\beta$; these values have commonly been interpreted as quantities proportional to a regional blood volume and a blood velocity, respectively, while the value $A\beta$ has been interpreted as a quantity proportional to the flow.

Parametric imaging techniques are also commonly used for graphically representing the result of the above-described quantitative analysis. For this purpose, a parametric image is built by assigning the corresponding value of a selected perfusion parameter to each pixel. Typically, different ranges of values of the perfusion parameter are coded with corresponding colors; the pixel values so obtained are then overlaid on an original image. The parametric image shows the spatial distribution of the perfusion parameter throughout the body part under analysis; this facilitates the identification of possible portions of the body part that are abnormally perfused (for example, because of a pathological condition).

However, the parametric image simply provides a static representation of the values of the perfusion parameter. Therefore, it does not allow a direct visual perception of the perfusion process, which is normally provided by the playback of the original sequence of images.

A different approach is proposed in US Publication No. 2003/0114759, which is incorporated by reference. In this case, multiple single-phase sequences of images are built; each single-phase sequence is obtained by assembling all the images that were acquired at a corresponding phase of different cardiac cycles. For each single-phase sequence of images, the corresponding pixel values (or groups thereof) are fitted by a model function as above; a parametric image is again built by assigning the corresponding values of a selected perfusion parameter (calculated from the model function) to each pixel. The sequence of parametric images so obtained (for the different phases of the cardiac cycle) may be displayed in succession. The cited document also hints to the possibility of using the same technique for other organs that are not strongly related to the heart cycle (such as the liver, the kidney, a transplanted organ or a limb of the body). In this case, the above-described procedure is applied to different periods of the diagnostic process; for each period, a distinct parametric image is likewise generated from the corresponding sub-sequence of images (with these parametric images that may again be displayed in succession). In any case, the perfusion parameters are still formed using the values A, β and their combinations (such as A*β or A/β); alternatively, it is also possible to base the perfusion parameters on the error or variance of the corresponding model function.

The above-described solution provides some sort of indication of the perfusion changes at the different phases of the heart cycle (or more generally of the diagnostic process). Nevertheless, each parametric image is still based on fixed perfusion parameters representing the corresponding model function statically.

SUMMARY

In its general form, an embodiment of the present invention is based on the idea of representing animated perfusion images.

More specifically, an embodiment of the present invention proposes a medical imaging system (such as based on an ultrasound scanner). The system includes means for providing a sequence of recorded input images (for example, by extracting them from a storage device). Each input image offers a digital representation (at a corresponding instant) of a body part that was perfused with a contrast agent; particularly, each input image includes a plurality of visualizing values (such as a matrix of pixel/voxel values), each one representing a corresponding portion of the body part. Means is provided for associating each sequence of corresponding sets in the input images (each one including either a single visualizing value or a group thereof) with a model function of time (for example, through a curve-fitting process). The system further includes means for generating a sequence of computed images at further instants. Each computed image includes a plurality of further visualizing values; each one of these further visualizing values is determined by an instantaneous function-value, which is calculated from the associated model function at the corresponding further instant. Means (such as a monitor) is then provided for displaying the sequence of computed images.

In an embodiment of the invention, a reference region is selected in the input images; a sequence of reference values is then determined, according to the instantaneous function-values of the corresponding reference models at each (further) instant. In this case, each (further) visualizing value for a different analysis region is set by combining the instantaneous function-value and the corresponding reference value.

For example, each reference value is set according to the average of the instantaneous function-values of the reference region (at the relevant instant).

Advantageously, each visualizing value of the computed image is obtained by subtracting the reference value from the corresponding instantaneous function-value.

In a proposed implementation, the instantaneous function-values (for the analysis region and/or the reference region) correspond to the values of the associated model functions at the relevant instants.

In another implementation, the same instantaneous function-values correspond to the integrals of the associated model functions (at the relevant instants).

In an alternative embodiment of the invention, the visualizing values of the computed image are set directly to the instantaneous function-values. As above, the instantaneous function-values may correspond either to the values or to the integrals of the associated reference models at the relevant instants.

The operation of associating the model functions may be performed at the level of single pixel values, voxel values, or groups thereof.

A way to further improve the proposed solution is of linearizing the input images, so as to make their visualizing values substantially proportional to a concentration of the contrast agent in the corresponding portions of the body part.

In a preferred implementation of the invention, the system displays a sequence of overlaid images (which are determined by overlaying the sequence of computed images on the sequence of input images).

As a further enhancement, each visualizing value in the computed images that does not reach a threshold value is reset (for example, to zero).

In addition or in alternative, the visualizing values for which a quality-of-fit index does not reach a further threshold value are likewise reset.

Advantageously, the computed images are generated by removing an offset from the model functions.

As a further enhancement, the visualizing values in the computed images are displayed with a color-coded representation.

In a specific embodiment of the invention, one or more input images may be discarded (for example, when they are not suitable for further analysis).

An embodiment of the proposed solution is particularly advantageous when the sequence of input images has a frame rate that is lower than the one of the sequence of computed images.

Preferably, in this case one or more further images are inserted into the sequence of input images (for example, by duplicating the ones at the closest instants), so that each computed image can be overlaid on a corresponding input image.

In a particular embodiment of the invention, the system also includes means (such as an imaging probe) for acquiring the input images in succession from the body part.

Typically, the imaging probe is of the ultrasound (linear- or phased-array) type.

Another embodiment of the present invention proposes a corresponding medical imaging method.

A further embodiment of the invention proposes a computer program for performing the method.

A still further embodiment of the invention proposes a product embodying the program.

BRIEF DESCRIPTION OF THE DRAWINGS

One or more embodiments of the invention, as well as further features and the advantages thereof, will be best understood by reference to the following detailed description, given purely by way of a non-restrictive indication, to be read in conjunction with the accompanying drawings.

DETAILED DESCRIPTION

Figure 1:
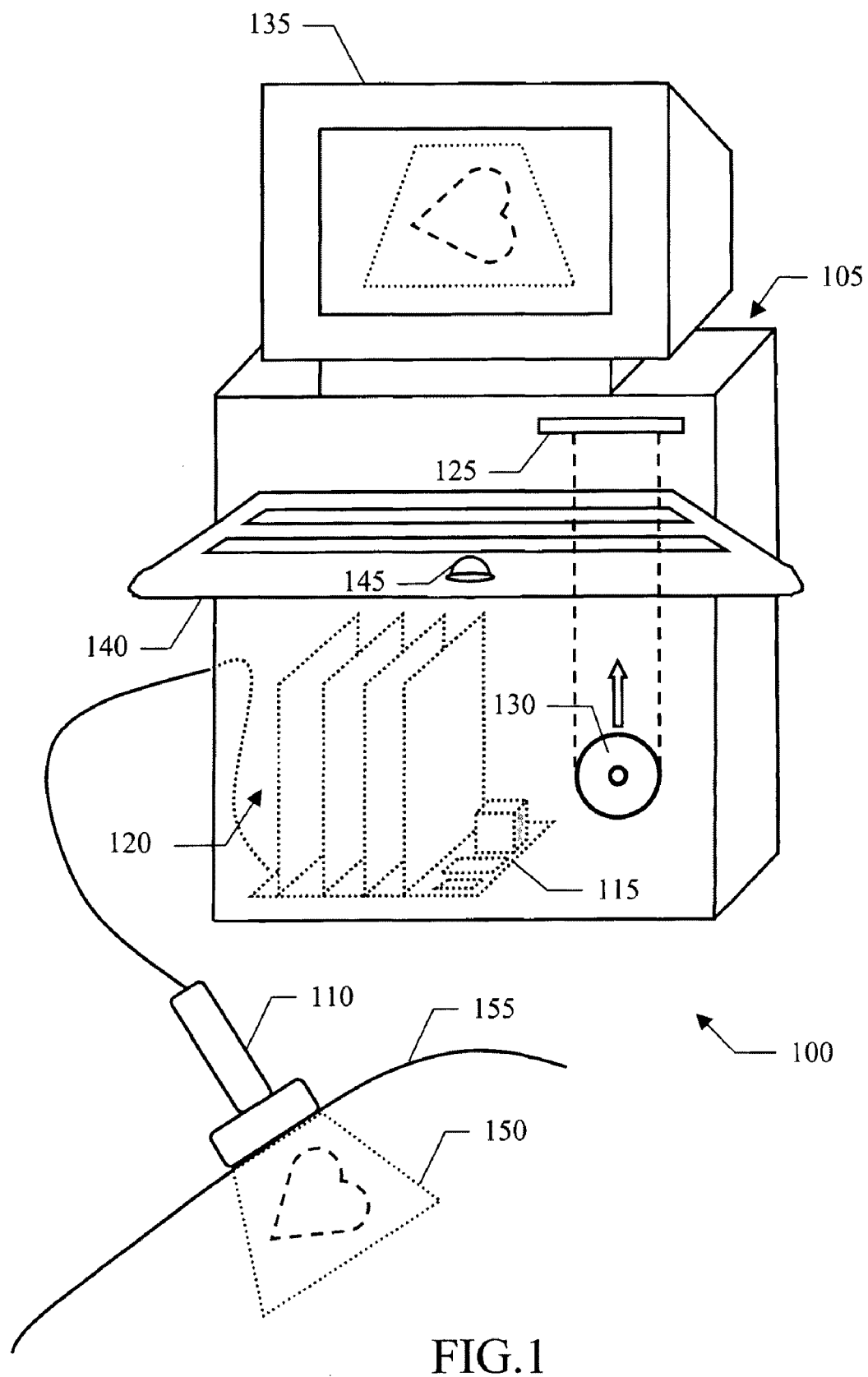
FIG. 1 is a pictorial representation of an ultrasound scanner in which the solution according to an embodiment of the invention is applicable.

With reference in particular to FIG. 1, a medical imaging system 100 is illustrated. Particularly, the system 100 includes an ultrasound scanner having a central unit 105 with a hand-held transmit-receive imaging probe 110 (for example, of the matrix-array type). The imaging probe 110 transmits ultrasound waves including a sequence of pulses (for example, having a center frequency between 2 and 10 MHz), and receives radio-frequency (RF) echo signals resulting from the backscattering of the ultrasound waves; for this purpose, the imaging probe 110 is provided with a transmit/receive multiplexer, which allows using the imaging probe 110 in the above-mentioned pulse-echo mode.

The central unit 105 houses a motherboard 115, on which the electronic circuits controlling operation of the ultrasound scanner 100 (such as a microprocessor, a working memory and a hard-disk drive) are mounted. Moreover, one or more daughter boards (denoted as a whole with 120) are plugged on the motherboard 115; the daughter boards 120 provide the electronic circuits for driving the imaging probe 110 and for processing the received echo signals. The ultrasound scanner 100 can also be equipped with a drive 125 for reading removable disks 130 (such as floppy-disks). A monitor 135 displays images relating to the analysis in progress. Operation of the ultrasound scanner 100 is controlled by means of a keyboard 140, which is connected to the central unit 105 in a conventional manner; preferably, the keyboard is provided with a trackball 145 that is used to manipulate the position of a pointer (not shown in the figure) on a screen of the monitor 135.

The ultrasound scanner 100 is used to assess blood perfusion in a body part 150 of a patient 155. For this purpose, a contrast agent is administered to the patient 155; the contrast agent may be provided either with a continuous administration (by means of a pump) or as a bolus (typically by hand with a syringe). Suitable contrast agents include suspensions of gas bubbles in a liquid carrier; typically, the gas bubbles have diameters on the order of 0.1-5 μm, so as to allow them to pass through the capillary bed of the patient 155. The gas bubbles are generally stabilized by entraining or encapsulating the gas or a precursor thereof into a variety of systems, including emulsifiers, oils, thickeners, sugars, proteins or polymers; stabilized gas bubbles are referred to as gas-filled microvesicles. The microvesicles include gas bubbles dispersed in an aqueous medium and bound at the gas/liquid interface by a very thin envelope involving a surfactant, i.e., an amphiphilic material such as phospholipids (also known in this case as microbubbles). Alternatively, the microvesicles include suspensions in which the gas bubbles are surrounded by a solid material envelope formed of natural or synthetic polymers (also known in this case as microballoons or microcapsules). Another kind of contrast agent includes suspensions of porous microparticles of polymers or other solids, which carry gas bubbles entrapped within the pores of the microparticles. Examples of suitable aqueous suspensions of microvesicles, in particular microbubbles and microballoons, and of the preparation thereof are described in EP-A-0458745, WO-A-91/15244, EP-A-0554213, WO-A-94/09829 and WO-A-95/16467 (the entire disclosures of which are herein incorporated by reference). A commercial ultrasound contrast agent comprising gas-filled microvesicles is SonoVue® by Bracco International BV.

The imaging probe 110 is placed in contact with the skin of the patient 155 in the area of the body part 150 to be analyzed. Typically, after a predetermined period (for example, a few seconds) ensuring that the contrast agent has filled the body part 150, one or more ultrasound pulses with high acoustic energy (flash) are applied; the acoustic energy is sufficient (such as with a mechanical index of 1-2) to cause the destruction of a significant portion of the contrast agent (for example, at least 50%); this allows the detection of a substantial variation of the received echo signal between the value measured right after the application of the destruction flash and when the body part is replenished by the contrast agent. A series of ultrasound pulses with low acoustic energy (such as with a mechanical index of 0.01-0.1) is then applied, so as to involve no further destruction of the contrast agent; observation of the replenishment (or reperfusion) of the contrast agent in the body part 150 provides information about the local blood perfusion. For this purpose, digital images representing the body part 150 are acquired continuously (for example, at a rate of 10-30 images per second), in order to track the evolution of the perfusion process over time.

Figure 2:
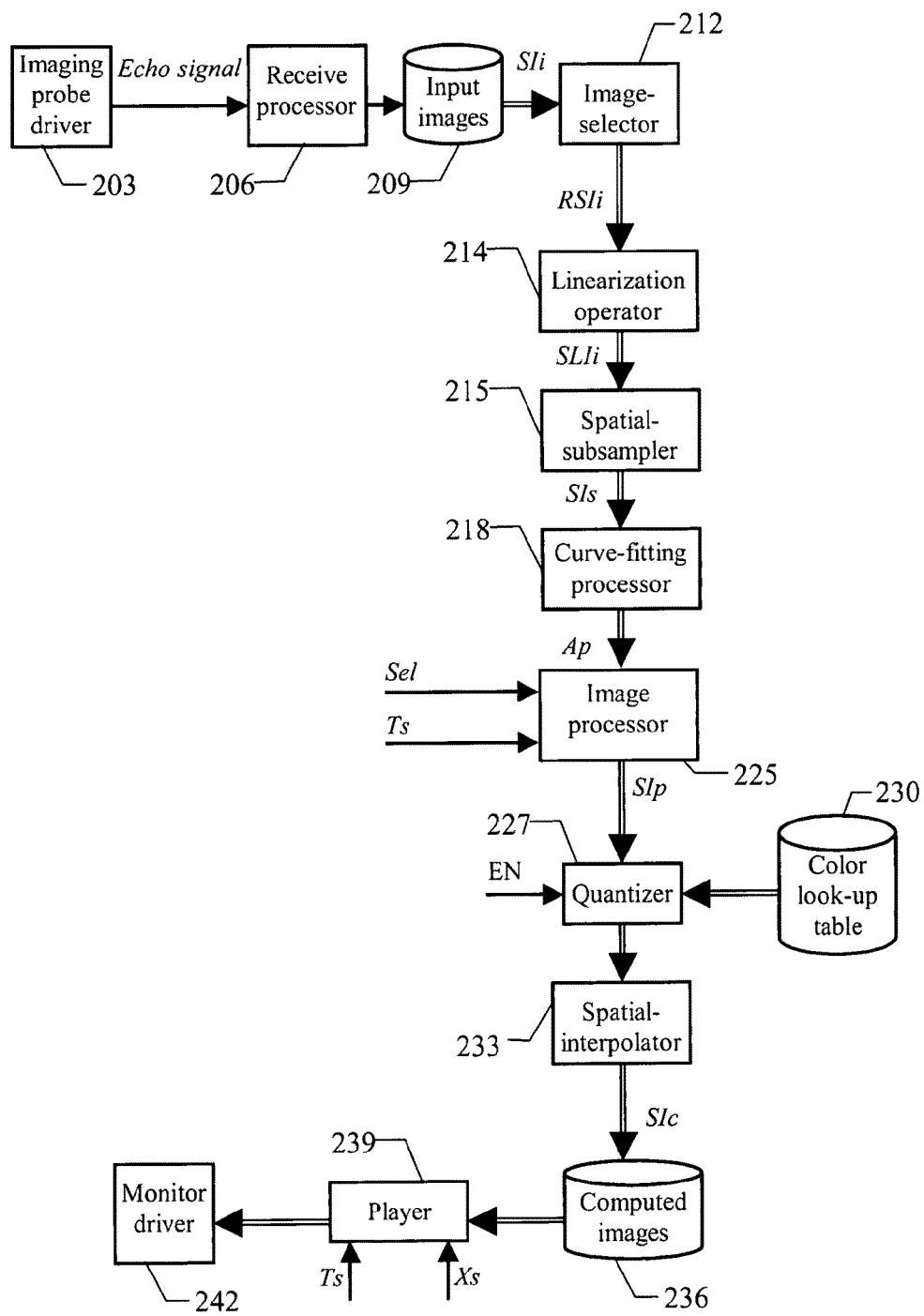
FIG. 2 depicts the main software and hardware components that can be used for practicing a solution according to an embodiment of the invention.

Moving now to FIG. 2, the main software and hardware components that can be used for practicing the solution according to a simplified embodiment of the invention are denoted as a whole with the reference 200. The information (programs and data) is typically stored on the hard disk and loaded (at least partially) into the working memory when the programs are running, together with an operating system and other application programs (not shown in the figure). For example, the programs can be initially installed onto the hard disk from CD-ROMs.

Particularly, a driver 203 controls the imaging probe (not shown in the figure); for example, the imaging probe driver 203 includes a transmit beam former and pulsers for generating the (pulsed) ultrasound waves to be applied to the body part under analysis. The corresponding (RF) echo signals that are received from said body part are supplied to a receive processor 206. Typically, the receive processor 206 pre-amplifies the RF echo signals and applies a preliminary time-gain compensation (TGC); the (analog) RF echo signals are then converted into digital values by an Analog-to-Digital Converter (ADC), and combined into focused RF echo signals through a receive beam former. The RF echo signals so obtained are preferably processed through further digital algorithms (such as algorithms specific for the enhancement of contrast-agent-based echo signals) and other linear or non-linear signal conditioners (such as a post-beam-forming TGC). The RF echo signals are then demodulated, log-compressed, and then scan-converted into a video format. This process results in the registration of a sequence of input images SIi, which are stored into a corresponding repository 209 for offline analysis. Each input image includes a digital representation of the body part during the perfusion process. The input image is defined by a matrix (for example, with 512 rows and 512 columns) of visualizing values; each visualizing value includes a value (for example, between 0 and 255) that is determined by the acoustic power of the echo signal relating to a basic picture element (pixel) or volume element (voxel) of the body part.

The sequence of input images SIi is extracted from the repository 209 and supplied to an image-selector 212. The image-selector 212 removes the input images (if any) that are not suitable for further analysis; for example, the image-selector 212 skips any input image that is misaligned (due to the motion of the patient, to his/her respiratory cycle or to the involuntary movement of the imaging probe) and whose motion cannot be compensated (for example, because of an "out-of-plane" movement).

The sequence of input images so reduced (denoted with RSIi) is provided to an operator 214, which linearizes each input image pixel-by-pixel. More specifically, the linearization operator 214 processes each pixel value so as to make it directly proportional to the corresponding local concentration of the contrast agent; this reflects the nature of the scattering of acoustic energy by a population of randomly spaced scatterers, which provides an echo-power signal proportional to the contrast agent concentration. For example, the result can be achieved by applying an inverse log-compression (to reverse the effect of its application by the receive processor 206), and then squaring the values so obtained (as described in WO-A-2004/110279, the entire disclosures of which is herein incorporated by reference). This operation generates a sequence of linearized input images denoted with SLIi.

The sequence of linearized input images SLIi is provided to a spatial-subsampler 215. The spatial-subsampler 215 partitions each linearized input image into cells corresponding to a spatial resolution of the imaging probe; each cell includes a group of adjacent pixels (or voxels), for example, ranging from 2 to 16 along each dimension of the linearized input images. The spatial resolution is determined automatically by estimating the smallest significant elements that can be discriminated in the linearized input images (consisting of the speckle grains that are typically visible in the input images in the case of the ultrasound scanner); for example, this result can be achieved through a spectral analysis of the sequence of linearized input images SLIi along each dimension. Each linearized input image is then replaced by a corresponding subsampled image, which represents each cell of the linearized input image with a single value defined by an average of its pixel values (for example, by subsampling the linearized input image after applying a low-pass filtering). This results in a sequence of subsampled images SIs, which is transmitted to a curve-fitting processor 218.

The curve-fitting processor 218 associates each cell of the subsampled images with an instance of a model function of time (t), which is selected according to the specific perfusion process to be represented. The instance of the model function is defined by the values of a set of parameters thereof. The parameter values are chosen as those that best fit the corresponding sequence of cell values (using well known error-minimization algorithms). The curve-fitting processor 218 thus generates a parameter matrix Ap, which contains the optimal values of these parameters for each cell.

The parameter matrix Ap is then input to an image processor 225, which is controlled by a selection signal Sel. The image processor 225 is specifically designed for calculating different types of instantaneous function-values of each model function according to the selection signal Sel (as described in detail in the following); examples of these instantaneous function-values are the actual value of the model function or its integral. The image processor 225 also receives a value defining a desired sampling interval Ts (for example, in the range 5-80 ms). The image processor 225 builds a sequence of processed images SIp. Each processed image is associated to a corresponding instant defined by the sampling interval Ts, with the j-th processed image (j>=0) that is associated to the instant $t_j=j \cdot Ts$ starting from the time origin of the perfusion process. For each cell, the processed image includes the value of the attribute of the corresponding model function at the relevant instant $t_j$.

The sequence of processed images SIp is provided to a quantizer 227, which is controlled by an enabling signal EN. The quantizer 227 converts the continuous values of the cells into corresponding discrete values (for example, consisting of 64 or 128 levels that are uniformly distributed between the lowest value and the highest value of all the cells). The quantizer 227 also accesses a color look-up table 230. The color look-up table 230 associates all the possible levels with the representation of corresponding colors (that are preferably brighter as the levels increase); for example, each color is defined by an index for accessing a location within a palette containing its actual specification. The quantizer 227 is enabled by asserting the signal EN; in this condition, it replaces each cell value in the processed images with the corresponding color representation. Conversely, when the quantizer 227 is disabled the sequence of processed images SIp passes through it without any change.

In any case, the sequence of processed images SIp (either quantized or as originally built) is provided to a spatial-interpolator 233. The spatial-interpolator 233 restores the full-size of the processed images (corresponding to the one of the input images) according to an interpolation method (such as based on the nearest neighbor, bilinear, or bicubic technique). More in detail, each processed image is converted into a corresponding computed image; for this purpose, the value of each cell in the processed image is replicated for the corresponding group of pixels (nearest neighbor interpolation method) and optionally filtered spatially (such as using a low-pass 2D or 3D spatial filter). The sequence of computed images SIc so obtained thus represents an animation of the perfusion process; these computed images are stored into a repository 236.

The repository 236 is accessed by a player 239, which also receives the sampling interval Ts (defining the time interval between each pair of adjacent computed images). In addition, the player 239 is supplied with an index Xs, which is selected according to the desired reproduction speed of the sequence of computed images SIc; for example, the speed index Xs is set to 1 for a reproduction in real time, to a value lower than 1 for a reproduction in slow-motion or to a value higher than 1 for a reproduction in accelerated-motion. The player 239 extracts the computed images in succession from the repository 239 at intervals given by Ts/Xs. Each computed image is then passed to a monitor driver 242 for its playback (according to this frame rate).

Figure 3:
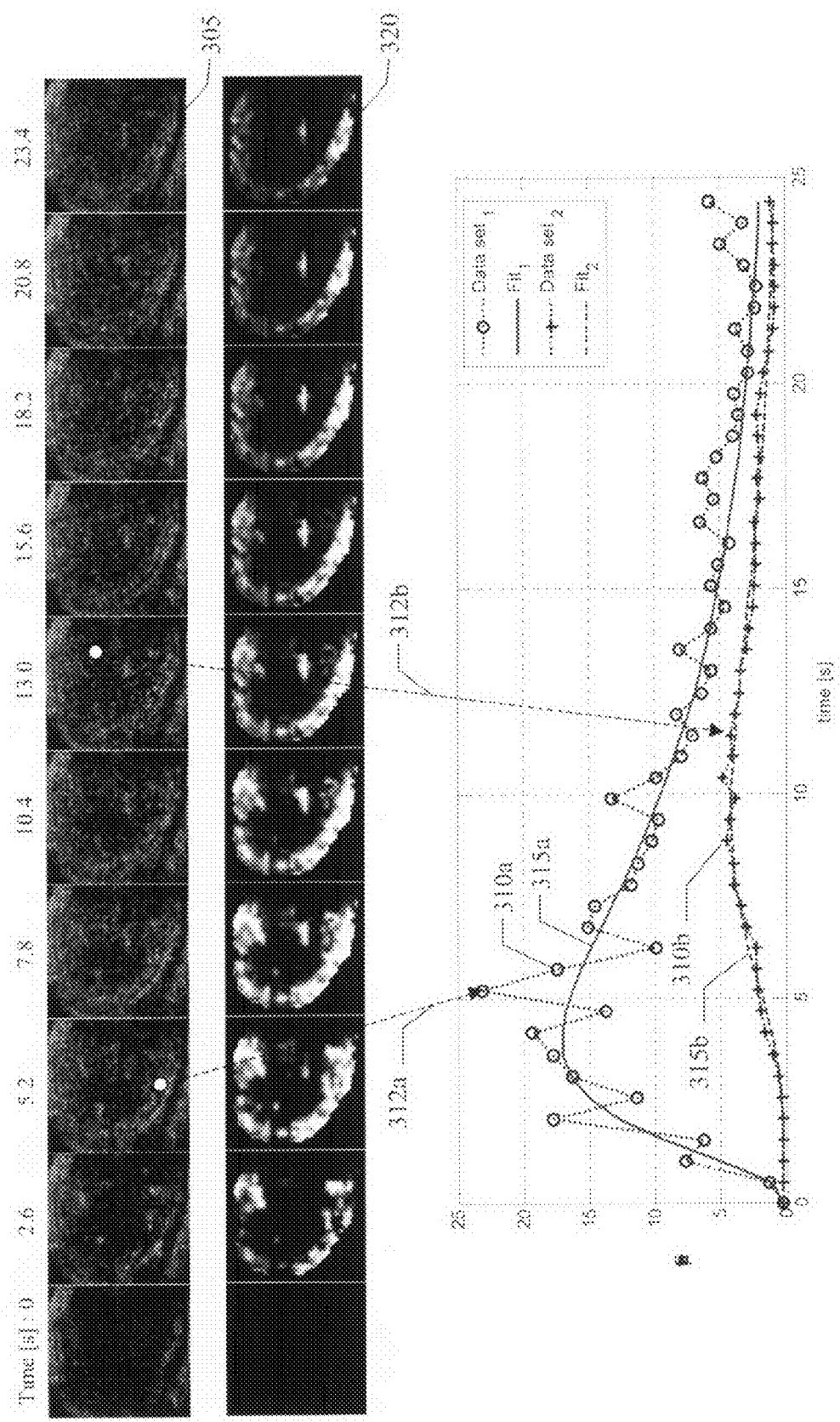
FIG. 3 shows an exemplary application of the solution according to this embodiment of the invention.

An exemplary application of the above-described solution is shown in FIG. 3. Particularly, this application relates to a bolus administration without any deliberate destruction of the contrast agent. A sequence of input images was acquired by the ultrasound scanner during the perfusion process of a mammary tumor; this sequence (shown as resulting after demodulation and log-compression) is denoted with 305. The input images were recorded at intervals of 0.52 s; for the sake of clarity, the sequence shown in the figure only includes a subset of the input images (more specifically, one input image every 2.6 s). As can be seen, the sequence of input images 305 depicts the evolution over time of the echo signal during the perfusion process. More specifically, in a wash-in phase following the administration of the contrast agent the echo signal increases (as the contrast agent washes into the body part) until a maximum level at around the time 4 s; the echo signal then starts decreasing in a wash-out phase of the contrast agent (extending over several tens of seconds). Each sequence of cell values in the corresponding linearized images (not shown in the figure) represents the echo-power signals, which were recorded for a corresponding portion of the body part over time. Two exemplary sequences of these cell values obtained by averaging the corresponding (linearized) pixel values are denoted in the figure with 310a (Data set$_1$) for the cell identified by the dashed arrow 312a and with 310b (Data set$_2$) for the cell identified by the dashed arrow 312b.

For each cell, the sequence of corresponding values is fitted by an instance of a suitable model function (defined by the values of the respective parameters). In the example at issue, the model function consists of a lognormal distribution function (i.e., a normal distribution function of the natural logarithm of the independent variable t):

$$B(t) = O + A \cdot \frac{e^{-\frac{[ln(t-t_0)-m_B]^2}{2s_B^2}}}{(t-t_o) \cdot s_B \sqrt{2\pi}} \quad \text{for } t - t_0 > 0, \text{ and}$$

$$B(t) = O \quad \text{for } t - t_0 \leq 0,$$

where $t_0$ represents a delay depending on the choice of a time origin for the analysis of the perfusion process, O is an offset parameter and A is an amplitude parameter (which can be related to the relative regional tissue blood volume); in addition, the parameters $m_B$ and $s_B$ are the mean and standard deviation of the distribution of the natural logarithms of t, respectively. The graphical representations of the model functions associated with the sequences of cell values 310a and 310b are denoted in the figure with 315a (Fit$_1$) and 315b (Fit$_2$), respectively.

In this case, the instantaneous function-values (which are used to generate the computed images) correspond to the values of the model functions over time. More specifically, for each cell the respective values are calculated by evaluating the corresponding model function at the subsequent instants $t_j$. Each resulting sequence of cell values then represents the evolution over time of the echo-power signals (for a corresponding portion of the body part) as defined by the respective model function, instead of the actual echo-power signals that were recorded during the perfusion process (provided by the sequence of values for the same cell in the linearized input images). An exemplary sequence of computed images built as described above (at the same instants as the input images) is denoted with 320.

As clearly shown in the figure, the sequence of computed images 320 allows a strongly enhanced perception of the perfusion process, and especially of its pattern and kinetics (as compared to the sequence of input images 305). Several factors contribute to this enhanced perception. A first factor is due to the temporal smoothing in each cell of the local intensity associated with the presence of the contrast agent. A second factor is due to the spatial smoothing of the same intensity from cell to cell (which removes any rapid fluctuation of the speckle grains in time). Yet a third factor is due to the removal of any residual or cyclic movement among the input images. Indeed, for each cell, the corresponding values are computed at fixed locations by definition; therefore, any motion may degrade the quality of the fitting by the model functions, but it does not appear as motion in the sequence of computed images 320.

Preferably, the evaluation of the model function for each cell of the computed images is performed by removing the offset parameter O. This efficiently suppresses the contribution of any background echo-power signal in the computed images. As a result, a significantly clearer perception of the dynamics of the perfusion process is achieved.

The reading of the sequence of computed images 320 is further facilitated when they are displayed in color (as defined by the color representations assigned to the cells during the process of building the computed images). In this case, each different color bears a quantitative meaning of its own; for example, this value can be read out from a color-bar (not shown in the figure), which is displayed on the monitor close to the sequence of computed images 320.

It is emphasized that the selection of the sampling interval Ts (defining the temporal resolution of the sequence of computed images) is entirely independent of the acquisition rate of the input images. Therefore, the computed images may be calculated at any instants (even when no input image is available in the original sequence); in this way, it is possible to optimize the sampling interval Ts, in order to smooth the rendering of the computed images (allowing the best possible perception of the perfusion process, and especially of its kinetics and spatial distribution).

Figure 4:
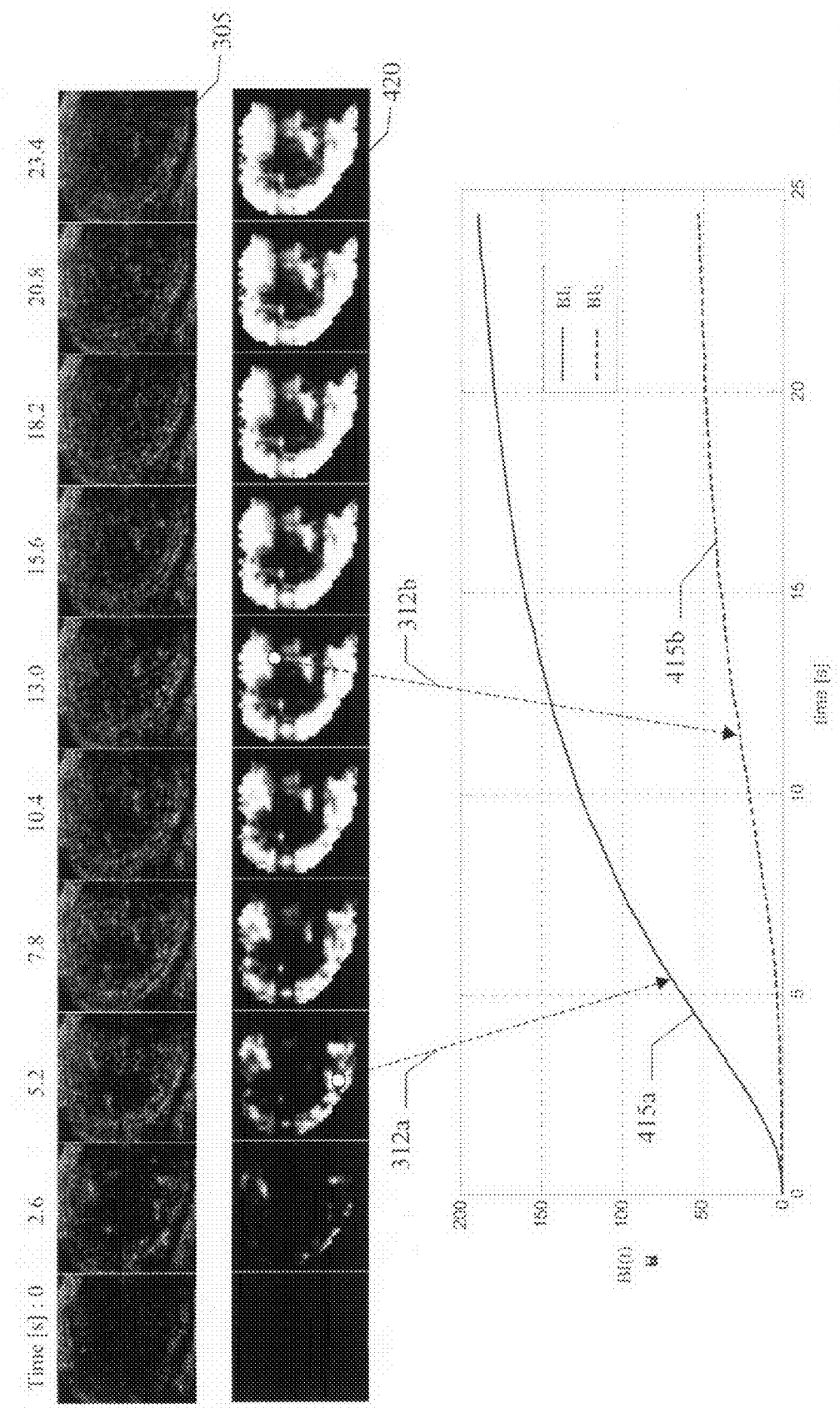
FIG. 4 shows a different exemplary application of the solution according to the same embodiment of the invention.

With reference now to FIG. 4, an exemplary application of the above-described solution to the same sequence of input images 305 is shown for the selection of a different type of instantaneous function-value (according to the corresponding signal Sel). In this case, the instantaneous function-values correspond to the integrals of the model functions over time. More specifically, for each cell the respective values are calculated by integrating the model function B(t) minus the offset parameter O from the time origin to the subsequent instants $t_j$. These values, denoted with BI($t_j$), represent a quantity proportional to the amount of contrast agent that had flowed through the portion of the body part represented by the cell:

$$BI(t_j) = \int_0^{t_j} [B(t) - O] dt.$$

The graphical representations of the instantaneous values of that integral for the cell identified by the dashed arrow 312a and for the cell identified by the dashed arrow 312b are denoted in the figure with 415a (BI$_1$) and 415b (BI$_2$), respectively. An exemplary sequence of computed images built as described above (at the same instants as the input images) is denoted with 420.

In this case, the sequence of computed images 420 provides an animated representation of the evolution over time of any attribute of interest. Moreover, as pointed out in the preceding application, the sequence of computed images 420 provides an enhanced visual perception of the perfusion process (due to the temporal smoothing, the spatial smoothing, and the motion removal). Likewise, the subtraction of the offset parameter O suppresses the contribution of any background echo-power signal. In addition, the reading of the sequence of computed images 420 can be further facilitated when they are displayed in color.

Figure 5:
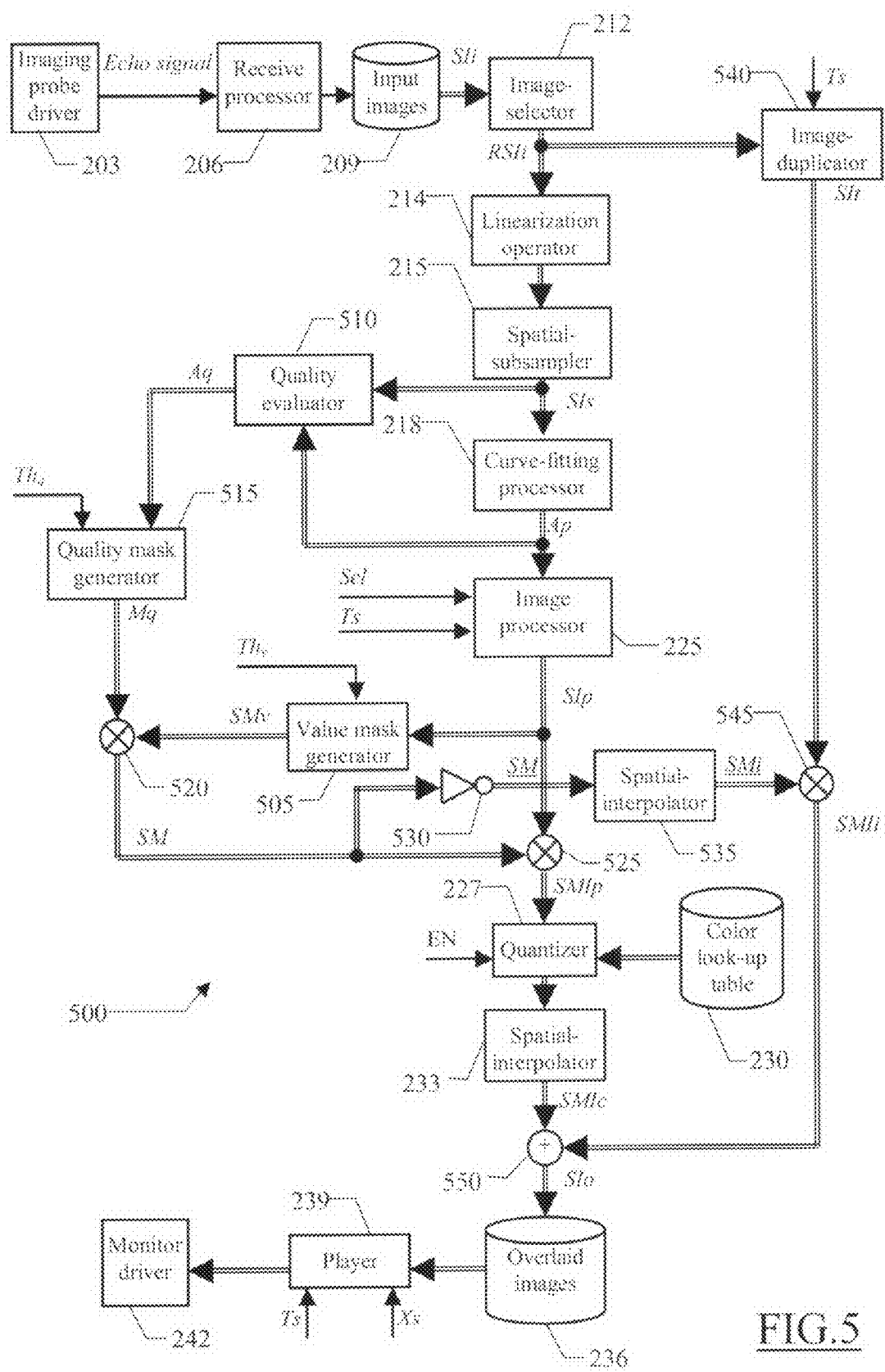
FIG. 5 depicts the main software and hardware components that can be used for practicing a solution according to another embodiment of the invention.

Moving now to FIG. 5, the main software and hardware components that can be used for practicing a solution according to another (more sophisticated) embodiment of the invention are denoted as a whole with the reference 500 (the elements corresponding to the ones shown in the FIG. 2 are denoted with the same references, and their explanation will be omitted for the sake of brevity).

In this case, the sequence of processed images SIp built by the image processor 225 (according to the selection signal Sel) is provided to a value mask generator 505; the value mask generator 505 also receives a predefined threshold value Th$_v$ for the cell values (for example, from 0 to 5% of a maximum allowable value). The value mask generator 505 creates a sequence of value masks SMv. Each value mask is obtained from the corresponding processed image by assigning (to each cell) the logic value 1 if its value is strictly higher than the threshold value $Th_v$ or the logic value 0 otherwise.

At the same time, the sequence of subsampled images SIs (from the spatial subsampler 215) and the parameter matrix Ap (from the curve-fitting processor 218) are supplied to a quality evaluator 510. For each cell, the quality evaluator 510 determines a Quality of Fit (QOF) index indicative of the quality of the curve-fitting process applied by the module 218; for example, the QOF index may be defined as a percentage:

$$QOF = 100 \cdot \left(1 - \frac{SSE}{SST}\right),$$

where the terms SSE and SST are calculated as follows. Particularly, the term SSE is the sum of the squares of the differences between the values in the subsampled images and the corresponding (predicted) values of the model function; in other words, indicating with $S_i$ the cell value in the subsampled image, corresponding to the input image acquired at the instant $t_i$ (with $i=1 \ldots N$), and with $P_i$ the value of the model function at the same instant $t_i$, we have:

$$SSE = \sum_{i=1}^{N} (S_i - P_i)^2,$$

The term SST is the sum of the squares of the differences of the same values of the subsampled images from their mean value (AVG):

$$SST = \sum_{i=1}^{N} (S_i - AVG)^2, \text{ with } AVG = \frac{1}{N} \cdot \sum_{i=1}^{N} S_i.$$

It is then evident that the higher the QOF index, the more accurate the curve-fitting process (up to the ideal value of 100% for a perfect matching of the model function to the available information).

The quality evaluator 510 thus generates a quality matrix Aq, which includes the corresponding QOF index for each cell. The quality matrix Aq is passed to a quality mask generator 515, which also receives a predefined threshold value $Th_q$ for the QOF indexes (for example, between 40% and 60%). The quality mask generator 515 converts the quality matrix Aq into a corresponding quality mask Mq; for this purpose, the quality mask generator 515 assigns (to each cell) the logic value 1 if its QOF index is strictly higher than the threshold value $Th_q$ or the logic value 0 otherwise.

A multiplier operator 520 receives the sequence of value masks SMv (from the value mask generator 505) and the quality mask Mq (from the quality mask generator 515). The operator 520 multiplies each value mask by the quality mask Mq cell-by-cell, so as to generate a sequence of corresponding (total) masks SM. In this way, each cell of the masks so obtained will have the logic value 0 if the cell value of the respective processed image is lower than the threshold value $Th_v$ or if the corresponding QOF index is lower than the threshold value $Th_q$, and it will have the logic value 1 otherwise.

The sequence of masks SM is input to a further multiplier operator 525, which also receives the sequence of processed images SIp from the image processor 225. The operator 525 multiplies each processed image by the corresponding mask cell-by-cell, so as to obtain a sequence of masked processed images SMIp; as a result, each masked processed image only includes the cell values of the corresponding processed image that are higher than the threshold value $Th_v$ and whose QOF index is higher than the threshold value $Th_q$ at the same time (while the other cell values are reset to 0). The sequence of masked processed images SMIp is then provided to the quantizer 227, so as to obtain a corresponding sequence of masked computed images SMIc from the spatial interpolator 233 as described above.

The sequence of masks SM is also supplied to an inverter 530, which generates a corresponding sequence of inverted masks $\overline{SM}$ (by exchanging the logic values 0 and 1). The sequence of inverted masks $\overline{SM}$ is then provided to a further spatial-interpolator 535 (which acts identically to the spatial-interpolator 233) for restoring the full-size of the inverted masks (corresponding to the one of the input images). This process results in a sequence of interpolated inverted masks $\overline{SM}i$. At the same time, the reduced sequence of input images $\overline{RSI}i$ (generated by the image-selector 212) is provided to an image-duplicator 540 (in addition to the linearization operator 214); the image-duplicator 540 also receives the sampling interval Ts (defining the time interval between each pair of adjacent masked computed images). When the time interval between each pair of available input images is higher than the one of the masked computed images, the image-duplicator 540 adds one or more new images to the reduced sequence of input images RSIi by duplicating the closest input images as needed to match the number of input images to the number of computed images. This operation is aimed at having (for each masked computed image at the instant $t_j$) a corresponding input image acquired or duplicated at the same instant $t_j$. The sequence of synchronized input images so obtained (denoted with SIt) is input to a multiplier operator 545, which also receives the sequence of interpolated inverted masks $\overline{SM}i$ from the spatial-interpolator 535. The operator 545 multiplies each synchronized input image by the corresponding interpolated inverted mask pixel-by-pixel, so as to obtain a sequence of masked input images SMIi.

An operator 550 adds each masked computed image (from the spatial-interpolator 233) and the corresponding masked input image (from the multiplier operator 530) pixel-by-pixel, so as to obtain a sequence of overlaid images SIo. In this way, each pixel value of the input images is overridden by the corresponding value in the associated computed image if and only if the latter has a significant value (i.e., higher than the threshold value $Th_v$) and corresponds to an acceptably level of fit quality (i.e., its QOF index is higher than the threshold value $Th_q$). The sequence of overlaid images SIo is stored into the repository 236, and then provided to the player 239 that controls its playback as described before.

In this way, by tuning the threshold values $Th_v$, $Th_q$ it is possible to optimize the quality of the visualization with the minimum impact on the original images. Moreover, it should be noted that the application of the value masks and/or of the quality mask may be avoided by simply setting the threshold value $Th_v$ or the threshold value $Th_q$, respectively, to zero (so as to obtain corresponding all-one masks that do not affect the computed images).

Figure 6:
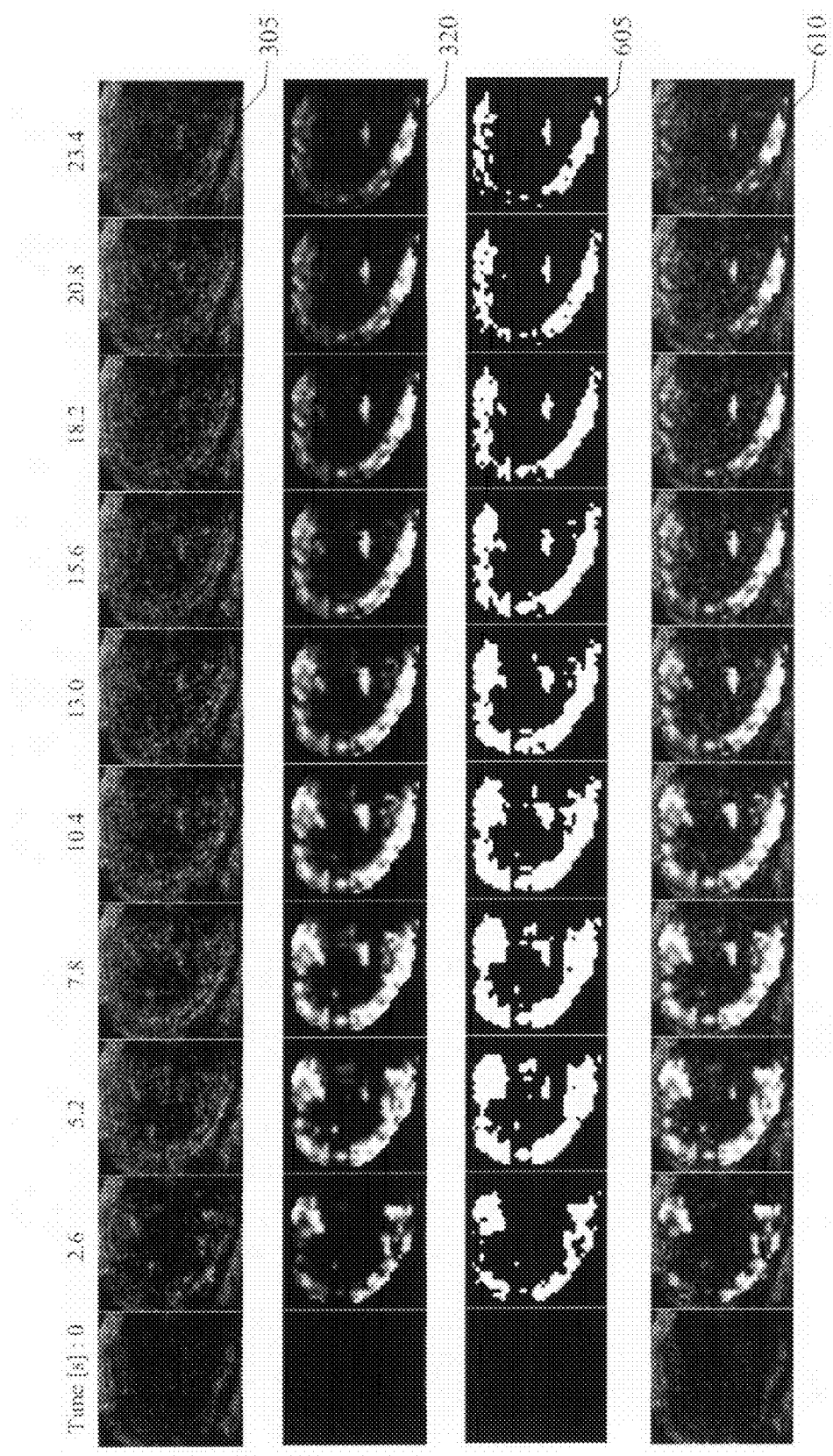
FIG. 6 shows an exemplary application of the solution according to this embodiment of the invention.

With reference now to FIG. 6, an exemplary application of the above-described solution to the same sequence of input images 305 is shown. Particularly, the sequence of computed images 320 described-above can be associated with a corresponding sequence of masks 605 (by setting the threshold value $Th_v$ to 1% of the maximum value in the sequence of processed images and the threshold value $Th_q$ to 0). The overlay of the computed images (multiplied by the corresponding masks) on the input images (multiplied by the corresponding interpolated inverted masks, not shown in the figure) generates a sequence of overlaid images 610. As clearly shown in the figure, the input images are still visible as a background; therefore, an enhanced visual perception of the perfusion process is provided. In this respect, it should be noted that the threshold value $Th_v$ defines the degree of overlay of the computed images; therefore, the suggested range of values (0-5%) preserves any significant information in the computed images and at the same time avoids overriding the original images when it is not strictly necessary. As a result, the sequence of overlaid images 610 provides an enhanced visual perception of the perfusion process (as noted in the preceding embodiment of the invention), which is now contextualized on the actual representation of the body part under analysis.

Figure 7:
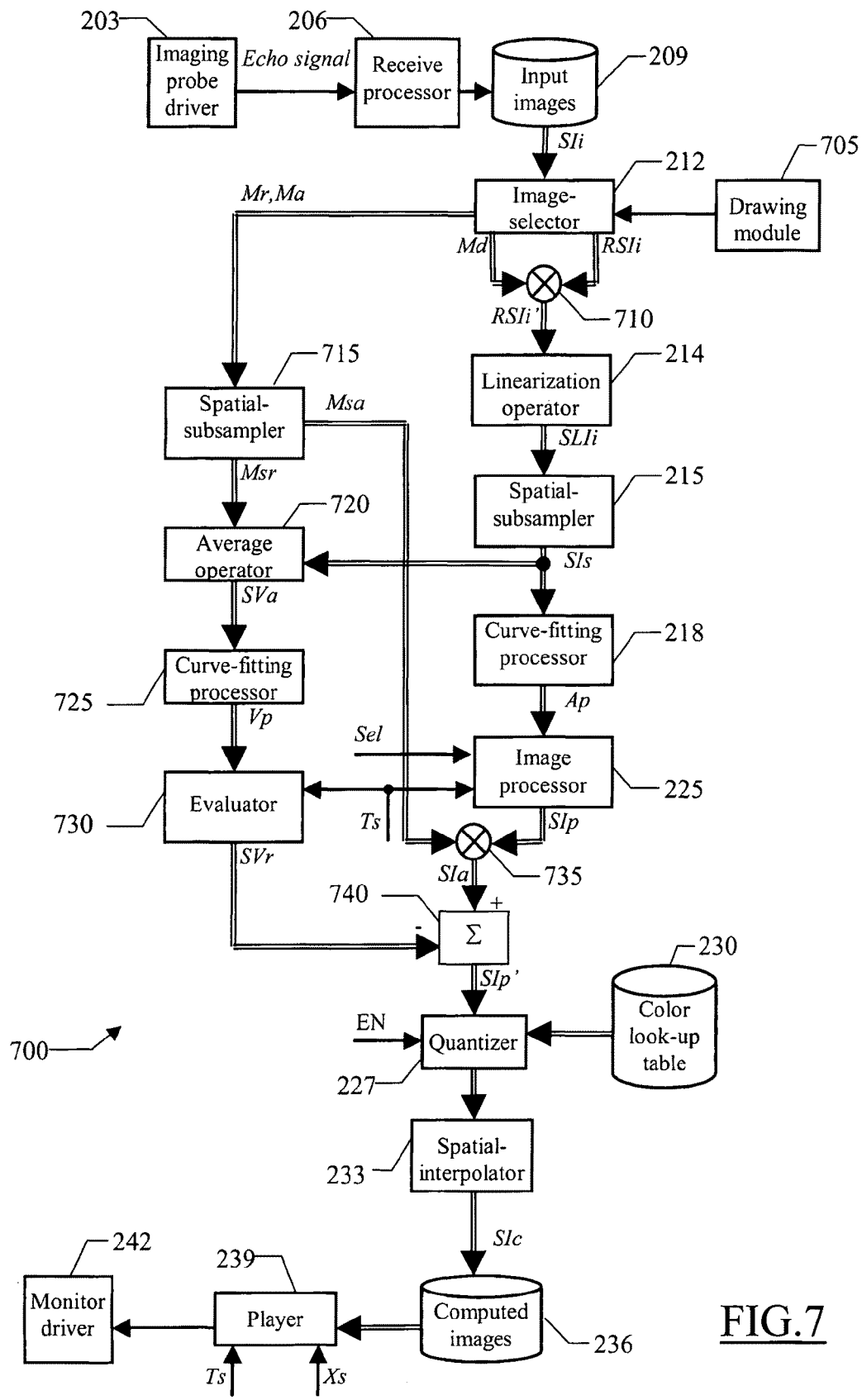
FIG. 7 depicts the main software and hardware components that can be used for practicing a solution according to a further embodiment of the invention.

Proceeding to FIG. 7, the main software and hardware components that can be used for practicing a solution according to a further embodiment of the invention are denoted as a whole with the reference 700. For the sake of simplicity, the additional features of this embodiment of the invention will be described with reference to the structure proposed in the FIG. 2 (wherein the corresponding elements are denoted with the same references and their explanation is omitted); however, it is expressly intended that the same features may be added to the more sophisticated implementation described above with reference to the FIG. 5.

Particularly, a drawing module 705 is used to define a reference region, a delimitation region and an analysis region on one of the input images, selected by the image selector 212 out of the repository 209. The reference region represents an area with well-defined characteristics (for example, outlining a tissue region deemed to be healthy); on the other hand, the delimitation region defines a region of interest (ROI) of the perfusion process (for example, outlining a tissue region deemed to be suspicious or known to be a lesion), whereas the analysis region defines a region that is chosen for analysis within the delimitation region. This operation generates a reference mask Mr (for the reference region), a delimitation mask Md (for the delimitation region), and an analysis mask Ma (for the analysis region). Each mask Mr, Md and Ma includes a matrix of binary values with the same size as the input images. In each of the three masks Mr, Md and Ma, the binary values inside their corresponding region are assigned the logic value 1, whereas the binary values outside their corresponding region are assigned the logic value 0.

A multiplier operator 710 receives the sequence of input images RSIi (reduced as described-above by the image selector 212) and the delimitation mask Md. The operator 710 multiplies each input image by the delimitation mask Md pixel-by-pixel, so as to reset all the pixel values that are outside the delimitation region to 0 (while the other pixel values remain unchanged). The reduced sequence of input images so updated (differentiated by the prime symbol, i.e., RSIi') is then provided to the linearization operator 214, so as to repeat the same operations described above. In this case, the sequence of processed images SIp built by the image processor 225 (for the whole delimitation region) is saved into a corresponding repository (not shown in the figure); therefore, the same information may be used (as described in the foregoing) for a different analysis region that is drawn inside the same delimitation region (without having to recalculate it).

The reference mask Mr and the analysis mask Ma are instead provided by the image selector 212 to a simplified spatial-subsampler 715. Particularly, the spatial-subsampler 715 partitions the reference mask Mr and the analysis mask Ma into a subsampled reference mask Msr and a subsampled analysis mask Msa, respectively (in a way similar to the spatial-subsampler 215 subsamples the linearized images); in this case, however, each cell value of the subsampled masks Msr and Msa is rounded off, so as to ensure that it always contains the values 0 or 1 only.

An average operator 720 receives the subsampled reference mask Msr and the sequence of subsampled images SIs (from the spatial subsampler 215). The average operator 720 generates a corresponding sequence of average values SVa. For this purpose, the average operator 720 multiplies each subsampled image by the subsampled reference mask Msr cell-by-cell. For each subsampled image, the values thus obtained are added in a buffer; the corresponding average value is then obtained by dividing the final value of the buffer by the number of non-zero values in the subsampled reference mask Msr; in this way, each average value includes the average of the cell values of the reference region in the corresponding subsampled image.

A further curve-fitting processor 725 (exactly the same as the curve-fitting processor 218) associates the sequence of average values SVa with an instance of the relevant model function (defined by the values of its parameters); the curve-fitting processor 725 thus generates the optimal values of these parameters (for the whole reference region), denoted with Vp. The parameter values Vp are input to an evaluator 730, which also receives the sampling interval Ts (defining the time between each pair of adjacent processed images). The evaluator 730 generates a sequence of reference values SVr, which is synchronized with the sequence of processed images SIp built by the image processor 225; more specifically, for each instant $t_j=j \cdot Ts$ the evaluator 730 sets the reference value to the corresponding instantaneous value of the model function defined by the parameter values Vp.

In parallel, a multiplier operator 735 receives the subsampled analysis mask Msa (from the spatial subsampler 715) and the sequence of processed images SIp (from the image processor 225). The operator 735 multiplies each processed image by the subsampled analysis mask Msa cell-by-cell, so as to generate a sequence of corresponding analysis images SIa; in this way, each analysis image only includes the cell values of the corresponding processed image that are inside the analysis region (defined by the subsampled analysis mask Msa), while the other cell values are reset to 0.

A subtraction operator 740 receives the sequence of analysis images SIa (from the multiplier operator 735) and the sequence of reference values SVr (from the evaluator 730), which are synchronous to each other. The operator 740 subtracts, for each instant in the sequence of analysis images SIa, the reference value from each of the cell values of the corresponding analysis image; this operation results in a sequence of corresponding updated processed images, which are differentiated by the prime symbol (i.e., SIp'); the sequence of processed images SIp' is provided to the quantizer 227 to repeat the same operations described in the foregoing.

A proposed embodiment of the invention advantageously enhances any differences in perfusion kinetics of the analysis region of the body part under examination, compared to the perfusion kinetics of the reference region; this strongly facilitates the identification of several pathologies. For example, this approach is particularly useful for the enhanced characterization of dynamic vascular patterns (DVP) in liver diseases. Indeed, several liver diseases may induce different perfusion kinetics of the contrast agent, which in general differ from the perfusion kinetics observable in normal parenchyma. These different kinetics can be appreciated, for instance, during the wash-in and wash-out phases of the contrast agent provided with a bolus administration.

Figure 8:
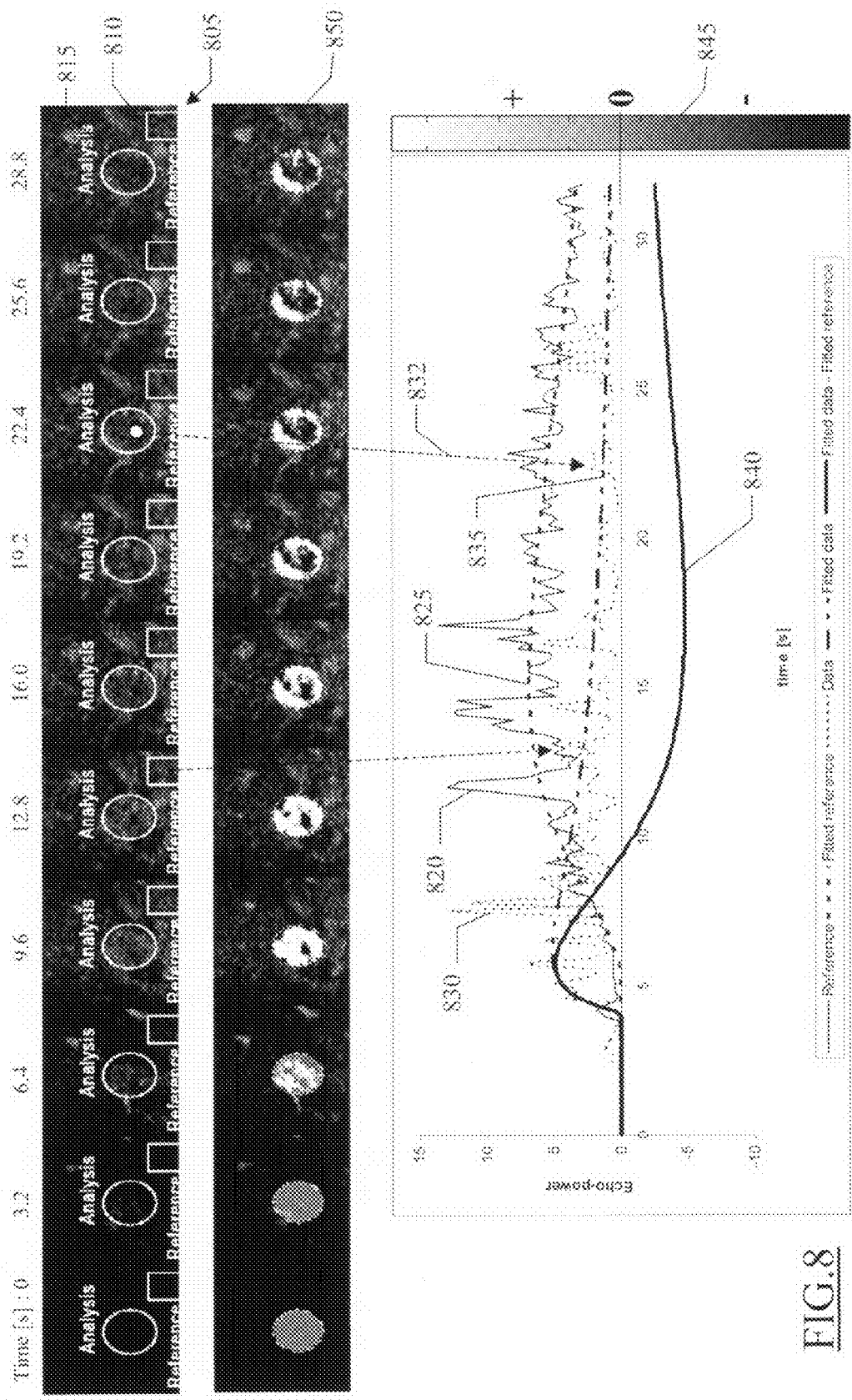
FIG. 8 shows an exemplary application of the solution according to this embodiment of the invention.

An exemplary application of the above-described solution is shown in FIG. 8. Particularly, this application again relates to a bolus administration without any deliberate destruction of the contrast agent. A sequence of input images was acquired by the ultrasound scanner during the perfusion process of a liver with a hypervascular metastasis; this sequence, shown as resulting after demodulation and log-compression, is denoted with 805 (for the sake of simplicity, only one input image every 3.2 s is illustrated). A reference region 810, deemed to represent normal parenchyma, is drawn by an operator in one selected input image (and reproduced in every other input image in this example); the operator also selects an analysis region 815, which identifies and delimits a suspected hypervascular metastasis.

Curve 820 (Reference) represents the sequence of reference values that are obtained by averaging the (linearized) pixel values of the sequence of input images 805 in the reference region 810. This sequence of reference values is fitted by an instance of a suitable model function (including the lognormal distribution function in the example at issue); the corresponding graphical representation is denoted in the figure with 825 (Fitted reference). The figure also shows a curve 830 (Data), which represents an exemplary sequence of cell values obtained by averaging the corresponding linearized pixel values for a cell identified by a dashed arrow 832 within the analysis region 815. This sequence of cell values is fitted by another instance of the same model function, whose graphical representation is denoted in the figure with 835 (Fitted data).

In this case, the computed images are generated by calculating (at each cell) the value of the corresponding model function minus the reference value at the same instant. For example, again considering the cell identified by the dashed arrow 832, the desired values are calculated by subtracting the model function 825 from the model function 835; a curve representing the sequence of these cell values is denoted in the figure with 840 (Fitted data—Fitted reference).

As can be seen, the result of the operation may be positive or negative, depending on the instantaneous values of the two model functions 825 and 835. Particularly, their difference is about zero when the value of the model function 835 (for the analysis region) is substantially the same as the corresponding reference value (i.e., the same as the average of the pixel values in the reference region at the same instant); conversely, the difference is positive when the value of the model function 835 is higher than the corresponding reference value, or it is negative otherwise. The cell values obtained as indicated above are then displayed according to a bi-polar palette look-up table 845 (of the gray-scale type in the example at issue). Therefore, each cell value is at an intermediate gray level when the value of the model function 835 is substantially the same as the corresponding reference value; on the other hand, the pixel is brighter or darker when the value of the model function 835 is higher or lower, respectively, than the corresponding reference value. An exemplary sequence of computed images built as described above (at the same instants as the input images) is denoted with 850.

In the example at issue, the hypervascular metastatis appears in brighter levels of gray at early times (between 4 s and 9 s), turning into darker levels later on (after roughly 10 s). This behavior clearly differs from the one of a region in normal parenchyma, wherein the pixels would have remained at the intermediate gray level. Therefore, imaging the liver according to the present embodiment of the invention makes the DVPs of different liver lesions much more conspicuous than when shown unprocessed.

Modifications

Naturally, in order to satisfy local and specific requirements, a person skilled in the art may apply to the solution described above many modifications and alterations. Particularly, although one or more embodiments of the present invention have been described with a certain degree of particularity, it should be understood that various omissions, substitutions and changes in the form and details as well as other embodiments are possible; moreover, it is expressly intended that specific elements and/or method steps described in connection with any disclosed embodiment of the invention may be incorporated in any other embodiment as a general matter of design choice.

Particularly, similar considerations apply if the ultrasound scanner has a different structure or includes other units. In addition, it is possible to use equivalent contrast agents or the body part may be perfused in another way (with either the destruction flash or not). Likewise, the images can have a different format, or the pixels can be represented with other values; alternatively, it is also possible to take into account a portion of the matrix of pixel values only (or more generally any other plurality of visualizing values).

Moreover, the principles of the one or more embodiments of the invention should not be limited to the described model functions; for example, in a perfusion process with a destruction flash it is possible to fit the sequence of corresponding cell values by an S-shape function (as described in WO-A-2004/110279, the entire disclosure of which is herein incorporated by reference), or by a mono-exponential function (as described in the cited article by Wei et al.), and the like.

Of course, any other equivalent technique for associating the suitable instance of the model function with each sequence of cell values is tenable (such as based on neural networks). Moreover, even though one or more embodiments of the present invention have been described in the foregoing with specific reference to offline analysis of the available information, their application in real-time is not excluded. For example, in a different implementation of an embodiment of the invention the input images are processed as soon as a sub-set of them allowing a significant curve-fitting is available (for example, including 7-12 input images, such as 10). Afterwards, each cell of this sub-set of input images is associated with the corresponding instance of the chosen model function; this allows calculating a first computed image (at the beginning of the process), which is preferably overlaid on the first input image. This first computed image so obtained may now be displayed as above, with a slight delay with respect to the actual acquisition instant of the corresponding input image (i.e., assuming an acquisition rate of the input images equal to 10 Hz, after 10/10 Hz=1 s in the example at issue). From now on, the same operation is continuously repeated for any new input image that is acquired. For this purpose, the model functions are recalculated at every iteration of the process according to the new information available. This result may be achieved taking into account all the input images so far acquired (thereby providing the highest possible accuracy); alternatively, the curve-fitting process is always applied only to the last 10 input images available (thereby increasing the processing speed but at the cost of reduced accuracy). In both cases, the model function preferably takes the form of cubic-spline filtering or median filtering, so as to make the computational complexity of the curve-fitting process acceptable even for real-time applications.

Similar considerations apply if the computed images (or the overlaid images) are printed, or more generally displayed in any other form.

Alternatively, it is possible to select the reference region and/or the analysis region with different procedures, or the reference region may be chosen according to other criteria; moreover, it is evident that the definition of the delimitation region is not strictly necessary, and it may be omitted in some implementations. Furthermore, the reference values may be determined with equivalent procedures. For example, although it is computationally advantageous to consolidate the pixel values of the reference region and then associate the resulting sequence of average values with a suitable instance of the desired model function (as described above), the possibility of inverting the order of these operations is contemplated. More in detail, all the cell values of the reference region may be associated with the corresponding model functions; for each instant, these model functions are evaluated and the average of the resulting values are then calculated.

In any case, nothing prevents consolidating the available information into the reference values with other algorithms (for example, by applying correlation, deconvolution or spectral analyses).

Moreover, the instantaneous function-values relating to the analysis region and the reference values may be combined in any other way (for example, by adding, multiplying, or dividing them).

Even though in the preceding description reference has been made to specific instantaneous function-values of the reference models, this is not to be intended as a limitation. For example, it is possible to base the instantaneous function-values for the analysis region, for the reference region or for both of them on the derivatives of the associated model functions; moreover, the possibility is not excluded of combining instantaneous function-values of different types. Similar considerations apply to the embodiments of the invention wherein the computed images are generated from the instantaneous function-values of the model functions directly (with no combination with any reference values). More generally, a solution according to an embodiment of the invention may also be used to represent the evolution over time of any other attributes or combination of attributes determined by whatever instantaneous function-values, which are calculated from the model functions at the relevant instants.

Optionally, the spatial-subsampler may partition each input image into cells that differ in size; for example, this result is achieved by means of a multi-scale analysis technique (such as a quadtree decomposition). However, the fitting by the desired model function may be applied on cells of arbitrary size (down to a single pixel/voxel).

Alternatively, the step of linearizing the input images may be omitted before spatial subsampling and curve-fitting, and a possibly different, more suitable, model function may be used in the curve-fitting processor in this case; in addition, it is possible to apply motion compensation to the sequence of input images to improve the accuracy of the fitting by the model functions.

Similar considerations apply if the computed images are overlaid on the input images with an equivalent algorithm. In any case, as described above, a simplified embodiment of the invention wherein the computed images are displayed directly (without being overlaid on the input images) is feasible.

In a different embodiment of the invention, the threshold value for building the value masks may be set to different values, or it may be determined dynamically on the basis of a statistical analysis of the cell values in the computed images.

Alternatively, it is possible to define the quality of the curve-fitting process with any other indicator (for example, a simple average of the corresponding differences); moreover, in this case as well the threshold value for building the quality mask may be set to different values (even determined dynamically).

Moreover, only the value masks or only the quality mask may be supported; in any case, the possibility of summing the whole computed images to the input images directly (without the use of any mask) is not excluded.

An implementation wherein the offset is not removed from the model function is also within the scope of one or more embodiments of the invention.

Similar considerations apply if the cell values in the processed images are partitioned in any other number of ranges (also non linearly distributed) for the association with the corresponding colors; moreover, it should be noted that the term color as used herein is also intended to include different tonalities, and any other visual clues. However, one or more embodiments of the present invention have equal application to black-and-white or grayscale representations of the computed images.

Alternatively, the selection of the input images to be discarded may be implemented with different algorithms (aimed at optimizing the accuracy of the fitting by the model functions). In any case, nothing prevents using all the available input images for fitting them by the model functions.

Likewise, other image-duplication techniques may be used for equalizing the rate of the sequence of input images with the one of the sequence of computed images, such as interpolation, extrapolation, or decimation. Without departing from the principles of one or more embodiments of the invention, the sequence of input images and the sequence of computed images may have arbitrary timing. However, the overlay of the computed images on the input images may also be implemented independently of their time synchrony.

In any case, the imaging probe may be of a different type (such as of the linear-, convex-, or phased-array type), or the input images may be acquired with another modality (for example, using Doppler-based algorithms). Alternatively, the medical imaging system includes an ultrasound scanner and a distinct computer (or any equivalent data processing entity); in this situation, the measured data is transferred from the ultrasound scanner to the computer for its processing (for example, through a removable disk, a memory key, or a network connection).

In any case, a solution according to an embodiment of the present invention lends itself to be used in any other medical imaging system, such as based on Magnetic Resonance Imaging (MRI) or X-ray Computed Tomography (CT).

Similar considerations apply if the program (which may be used to implement one or more embodiments of the invention) is structured in a different way, or if additional modules or functions are provided; likewise, the memory structures may be of other types, or may be replaced with equivalent entities (not necessarily consisting of physical storage media). Moreover, a proposed solution according to an embodiment of the invention lends itself to be implemented with an equivalent method (having similar or additional steps, even in a different order). In any case, the program may take any form suitable to be used by or in connection with any data processing system, such as external or resident software, firmware, or microcode (either in object code or in source code). Moreover, the program may be provided on any computer-usable medium; the medium may be any element suitable to contain, store, communicate, propagate, or transfer the program. Examples of such medium are fixed disks (where the program can be pre-loaded), removable disks, tapes, cards, wires, fibers, wireless connections, networks, broadcast waves, and the like; for example, the medium may be of the electronic, magnetic, optical, electromagnetic, infrared, or semiconductor type.

In any case, a solution according to an embodiment of the present invention lends itself to be carried out with a hardware structure (for example, integrated in a chip of semiconductor material), or with a combination of software and hardware.

The invention claimed is:

1. A medical imaging system including:
    means for providing a sequence of recorded input images each one offering a digital representation at a corresponding instant of a body part being perfused with a contrast agent, each input image including a plurality of visualizing values each one representing a corresponding portion of the body part,
    means for associating each sequence of corresponding sets in the input images of at least one visualizing value with a model function of time,
    means for generating a sequence of computed images at further instants, each computed image including a plurality of further visualizing values each one being determined by an instantaneous function-value which is calculated from the associated model function at the corresponding further instant, and
    means for displaying the sequence of computed images.

2. The system according to claim 1, wherein the means for generating the sequence of computed images includes means for selecting a reference region in the input images, means for generating a sequence of reference values at the further instants each one based on other instantaneous function-values being calculated from the model functions associated with the visualizing values of the reference region at the corresponding further instant, and means for setting each further visualizing value according to a combination of the instantaneous function-value and the reference value at the corresponding further instant.

3. The system according to claim 2, wherein the means for generating the sequence of reference values includes means for setting each reference value according to an average of the other instantaneous function-values at the corresponding further instant.

4. The system according to claim 2, wherein the means for setting each further visualizing value includes means for subtracting the reference value from the instantaneous function-value at the corresponding further instant.

5. The system according to claim 2, wherein each instantaneous function-value and/or each other instantaneous function-value corresponds to the value of the associated model function at the corresponding further instant.

6. The system according to claim 2, wherein each instantaneous function-value and/or each other instantaneous function-value corresponds to the integral of the associated model function at the corresponding further instant.

7. The system according to claim 1, wherein the means for determining the sequence of computed images includes means for setting each further visualizing value to the instantaneous function-value, the instantaneous function-value corresponding to the value of the associated model function at the corresponding further instant.

8. The system according to claim 1, wherein the means for generating the sequence of computed images includes means for setting each further visualizing value to the instantaneous function-value, the instantaneous function-value corresponding to the integral of the associated model function at the corresponding further instant.

9. The system according to claim 1, wherein each set of at least one visualizing value consists of a single pixel value, a single voxel value, a plurality of pixel values, or a plurality of voxel values.

10. The system according to claim 1, wherein the means for associating includes means for linearizing each input image to make each visualizing value thereof substantially proportional to a concentration of the contrast agent in the corresponding portion of the body part.

11. The system according to claim 1, further including:
    means for generating a sequence of overlaid images by overlaying the sequence of computed images on the sequence of input images, and
    means for displaying the sequence of overlaid images.

12. The system according to claim 11, wherein the means for generating the sequence of overlaid images includes means for resetting each further visualizing value not reaching a threshold value.

13. The system according to claim 11, wherein the means for generating the sequence of overlaid images includes:
    means for estimating an indicator of a quality of each association, and
    means for resetting each further visualizing value having the corresponding indicator not reaching a further threshold value.

14. The system according to claim 1, wherein the means for generating the sequence of computed images further includes means for removing an offset from the associated model function.

15. The system according to claim 1, wherein the means for generating the sequence of computed images further includes means for associating a plurality of predefined colors with corresponding ranges of values of the further visualizing values and means for replacing each further visualizing value with a representation of the corresponding color.

16. The system according to claim 1, wherein the means for providing the sequence of input images includes means for discarding at least one of the input images.

17. The system according to claim 1, wherein a rate of the sequence of input images is lower than a rate of the sequence of computed images.

18. The system according to claim 17, wherein the means for generating the sequence of overlaid images includes means for inserting at least one further input image into the sequence of input images to equalize the rate of the sequence of input images with the rate of the sequence of computed images, each computed image being overlaid on a corresponding input image.

19. The system according to claim 1, wherein the means for providing the sequence of input images includes means for acquiring the input images in succession from the body part.

20. The system according to claim 19, wherein the means for acquiring the input images includes means for transmitting ultrasound waves and for recording corresponding echo signals.

21. A medical imaging method including the steps of:
    providing a sequence of recorded input images each one offering a digital representation at a corresponding instant of a body part being perfused with a contrast agent, each input image including a plurality of visualizing values each one representing a corresponding portion of the body part, associating each sequence of corresponding sets in the input images of at least one visualizing value with a model function of time, generating a sequence of computed images at further instants, each computed image including a plurality of further visualizing values each one being determined by an instantaneous function-value which is calculated from the associated model function at the corresponding further instant, and displaying the sequence of computed images.

22. A non-transitory computer readable medium storing a computer program for performing the method of claim 21 when the computer program is executed on a data processing system.

23. A non-transitory computer readable medium storing a computer program, the computer program when executed on a data processing system causing the system to perform a medical imaging method, wherein the method includes the steps of:

providing a sequence of recorded input images each one offering a digital representation at a corresponding instant of a body part being perfused with a contrast agent, each input image including a plurality of visualizing values each one representing a corresponding portion of the body part, associating each sequence of corresponding sets in the input images of at least one visualizing value with a model function of time, generating a sequence of computed images at further instants, each computed image including a plurality of further visualizing values each one being determined by an instantaneous function-value which is calculated from the associated model function at the corresponding further instant, and displaying the sequence of computed images.

\* \* \* \* \*